(12) United States Patent
Velez-Rivera

(10) Patent No.: US 7,595,069 B2
(45) Date of Patent: Sep. 29, 2009

(54) PHYTO-COMPOSITION FOR THE TREATMENT OF JOINT DISEASES

(76) Inventor: Hector Velez-Rivera, Calzada Norte No. 5, Ciudad Granja, 45010, Zapopan, Jalisco (MX)

(*) Notice: Subject to any disclaimer, the term of this patent is extended or adjusted under 35 U.S.C. 154(b) by 71 days.

(21) Appl. No.: 10/594,439

(22) PCT Filed: Mar. 21, 2005

(86) PCT No.: PCT/IB2005/000762
§ 371 (c)(1), (2), (4) Date: Jul. 23, 2007

(87) PCT Pub. No.: WO2005/092355
PCT Pub. Date: Oct. 6, 2005

(65) Prior Publication Data
US 2007/0286899 A1  Dec. 13, 2007

(30) Foreign Application Priority Data
Mar. 26, 2004  (MX) ............... PA/A/2004002940

(51) Int. Cl.
*A61K 35/906* (2006.01)
*A61K 36/00* (2006.01)
(52) U.S. Cl. ........................ 424/756; 424/725
(58) Field of Classification Search .......... None
See application file for complete search history.

(56) References Cited

U.S. PATENT DOCUMENTS

| | | | |
|---|---|---|---|
| 4,666,701 A * | 5/1987 | Horrobin et al. | 514/558 |
| 4,888,326 A * | 12/1989 | Horrobin | 514/27 |
| 5,916,565 A | 6/1999 | Rose et al. | |
| 6,210,738 B1 * | 4/2001 | Chen | 426/597 |
| 6,238,696 B1 * | 5/2001 | Wang | 424/452 |
| 6,274,176 B1 | 8/2001 | Tomer et al. | |
| 6,497,889 B2 * | 12/2002 | Takekoshi et al. | 424/401 |
| 6,579,543 B1 * | 6/2003 | McClung | 424/728 |
| 2003/0069757 A1 * | 4/2003 | Greenberg | 705/2 |
| 2007/0154575 A1 * | 7/2007 | Shimoda et al. | 424/756 |

FOREIGN PATENT DOCUMENTS

| | | |
|---|---|---|
| FR | 2605224 A1 | 4/1988 |
| FR | 2633183 A1 | 12/1989 |
| FR | 2753374 A1 | 3/1998 |
| FR | 2806262 A1 | 9/2001 |
| WO | WO 99/20289 * | 4/1999 |

\* cited by examiner

*Primary Examiner*—Christopher R. Tate
(74) *Attorney, Agent, or Firm*—Browdy and Neimark, P.L.L.C.

(57) ABSTRACT

A phyto-composition is described for the treatment of joint diseases that comprises: a) from 0.01% to 26% in weight of an extract of *Curcuma longa* (turmeric); b) from 30% to 80% in weight of an extract of *Harpagophytum procumbens*, (devil's claws); c) from 0.01% to 25% in weight of an extract of *Filipendula ulmaria* (meadowsweet); and d) from 7% to 35% in weight of oil of *Oenothera biennis* (onagra). Said phyto-composition being used in combination with a pharmaceutically acceptable vehicle in order to obtain a pharmaceutical composition useful in the treatment of joint diseases, particularly, rheumatoid arthritis and osteoarthritis.

11 Claims, No Drawings

PHYTO-COMPOSITION FOR THE TREATMENT OF JOINT DISEASES

FIELD OF THE INVENTION

This invention relates to the techniques used in the pharmaceutical industry to obtain and manufacture natural medicaments, and more particularly, it relates to a phyto-composition for the treatment of joint diseases.

BACKGROUND OF THE INVENTION

Currently, joint diseases are a health problem that concerns the health authorities in charge of this industry because of the damage they produce, as well as because of the high percentage of population that suffers from them and the costs that the treatment of the affected patients creates for the health systems.

Joint diseases comprise around 100 different types in their classification, of which rheumatoid arthritis, osteoarthritis, fibromyalgia and gouty arthritis are the most frequent. The main symptoms that accompany these diseases are joint pain, inflammation, stiffness and progressive reduction in the functional capacity of the affected joints. Some types of arthritis, such as rheumatoid arthritis and lupus erythematosis, cause systemic damage in addition to the foregoing.

According to the statistical data of the World Health Organization (WHO), it is calculated that approximately 355 million people (6% of the world population) suffer from joint ailments. Particularly in the United States of America, 1 in every 6 individuals suffers from some joint disease, which means that there are 43 million people affected, holding first places among the existing pathologies in that country. Unfortunately, this figure is increasing more and more, and consequently, by the year 2020 it is expected that around 60 million people will be affected by some type of joint disease (1 in every 5 individuals).

In the United States of America joint diseases are also the main cause of disabilities in adults; these diseases limit the daily activities of more than 7 million persons, and by the year 2020 it is expected that there will be 12 million persons whose daily activities will be affected due to arthritic diseases.

Additionally, arthritis is related not only to disabilities that affect the individual, but this disease is also connected with a series of effects for the relatives and the health systems because, for example, in the United States of America 44 million doctors visits are due to problems related to arthritis, of whom 750,000 people require hospitalization. The estimated cost of this care is around 15 billion dollars and the total cost, including labor disabilities and rehabilitation costs, is 60 billion dollars.

Along with the economic cost, another cost must be mentioned, which is as or more important than the first one, and it is the emotional or psychological cost that joint disease represents to a person who has to put up continuously with the symptoms associated with these diseases such as pain, inflammation and progressive reduction in the functional capacity of their joints.

As mentioned previously, among the most important joint ailments is rheumatoid arthritis, which can be said to be a chronic, relapsing and systemic disease that affects principally the diarthrodial joints of the extremities and that are those that have the greatest movement. Arthritis presents more frequently in women than in men in a ratio of 3:1; the constitutional symptoms include general discomfort, fever and weight loss. The disease characteristically begins in the small joints of hands and feet, and progresses in a symmetrical, centripetal manner. In the elderly, the disease can present in the large, proximal joints and furthermore, in this disease, deformities are frequent.

Further, rheumatoid arthritis has manifestations outside the joints, such as vasculitis, atrophy of the skin and muscle, subcutaneous nodules, lymphadenopathy, splenomegaly and leucopoenia.

Rheumatoid arthritis is considered to be of unknown etiology, although a variety of evidence relates it to an autoimmune role which is directed especially against an inherent constituents of the synovial membrane.

There are various aspects that favor the inflammatory joint process in rheumatoid arthritis, including the presence of macrophages in the synovial infiltrate that because of their form and size, indicate that they are very active and secreting a large amount of cytokines that apparently are responsible for the tissue damage. Among these cytokines is the IL-1 (interleukin-1) and TNF-$\alpha$ (Tumor Necrosis Factor). These cytokines cause tissue damage directly or indirectly, since they induce activation of osteoclasts promoting bone resorption, induce the secretion of prostaglandin E that amplifies the bone resorption and increases the inflammatory process. Also, the cytokines induce chemotaxis of polymorphonuclears, macrophages and T-lymphocytes, encouraging their mobilization to the sites where the inflammatory reaction occurs.

Separately, TNF-$\alpha$ directly induces apoptosis of some cells locally, encouraging bone resorption and giving rise to the typical erosions of rheumatoid arthritis, and it also induces the secretion of other cytokines that also augment the inflammatory process.

As can be seen from the foregoing, the process of joint affectation in rheumatoid arthritis is created by several components of the immune system, where macrophages apparently have an important participation; it is because of this that some researchers in this field have proposed that this disease is induced mainly by macrophages.

With respect to osteoarthritis, also known as arthrosis, this is the most common degenerative joint disease. This ailment has been related to age. However, various investigations have demonstrated that although it is a process that affects older people more, it has nothing to do with the actual situation of wear and tear due to age. Osteoarthritis is characterized by the progressive loss of joint cartilage, reactive changes in the margins of the joints and in subchondral bone. The typical clinical manifestations of this disease consist in pain that gradually increases, rigidity and augmented joint volume with reduction in mobility.

Osteoarthritis develops in two conditions, the first of them presents when the biostructural properties of the cartilage and subchondral bone are normal, but the joint loads are excessive, producing tissue failure, and the second when the loads are adequate but the biostructural properties of the cartilage and bone are deficient. In this disease, the cytokines participate as mediators of the tissue damage, among which are found interleukin-1 (IL-1), interleukin-6 (IL-6) and the alfa tumor necrosis factor (TNF-$\alpha$).

As for the most commonly used treatments for joint diseases, we can mention that in the case of rheumatoid arthritis, the conventional pharmacological treatment consists in treating the patient in the most advanced, aggressive form possible, striving for the least toxicity. Something similar is done with osteoarthritis patients, except that this disease has a more prolonged evolution time than rheumatoid arthritis. In said traditional pharmacological treatment, DMDs (disease modifying drugs) are used, among which we find gold salts, synthetic anti-malaria drugs, immune-reducer agents or immunosuppressants and the anti-tumor necrosis factor (TNF) biological products, and interleukin (IL) inhibitors. The use of these medications, however, also causes adverse side effects in the patient, or else they are excessively expensive. For example, gold salts cause dermatitis and stomatitis, and furthermore have a metallic taste.

The anti-malaria drugs that have been being used for more than 50 years, and among which are hydroxychloroquine and chloroquine sulfate, cause cutaneous erosion, leucopoenia, peripheral neuropathy, and other adverse effects.

On this point, it is important to mention that methotrexate, which is the DMD used most at this time; this drug diminishes the production of interleukin-6, interleukin-8 and the alfa tumor necrosis factor, plus it has low toxicity. Nonetheless, it has been observed that 60% of patients who use methotrexate develop gastrointestinal problems such as diarrhea and nausea.

In relation to the biological agents, their objective is to interfere with the function of specific interleukins. Among these agents we can mention the chimeric monoclonal antibodies and the recombinant fusion proteins. The management strategies of these agents are directed to increasing the production of anti-inflammatory cytokines or inhibiting the pro-inflammatory cytokines. Still more, it has been observed that these agents have very good action and are not very toxic, but their cost is considerable.

So it is that in our times, there is a continual search for alternatives that effectively help in the treatment of joint diseases; for example, treatment has been sought with the use of phyto-medicaments or medicaments whose components include extracts of plant species.

The plant species include *Curcuma longa* (curcuma) and *Harpagophytum procumbens* (devil's claw) that have been used previously for trying to alleviate the inflammation present in joint diseases. Extracts are obtained from these species that are applied preferably by intramuscular and intraperitoneal route, exactly as described in the documents, "Pharmacology of *Curcuma longa*" by Hermann P. T. Ammon and Martin A. Wahl. 1990; "Anti-inflammatory and irritant activities of curcuma analogues in rats" by A. Mukhopadhyay, N. Basu, N. Ghatak and P. K. Gujral, 1982; and, "An Analytical Study, Anti-inflammatory and Analgesic Effects of H. P. and H. Zeyheri" by B. Baghdikiah, M. C. lanhers, J. Fleurentin, E. Ollivier, C. Maillard, 11:30 G. Balansard, and F. Mortzer. Said forms of application cause discomfort to patients in comparison with an oral administration form, and yet, the documents mention that oral administration does not achieve important effects such as the recovery of joint mobility and reduction in the time that they are stiff and swollen, which effects are in all respects desirable to attain not just for phyto-medicaments but also for the DMDs mentioned above.

In the state of the art, we can likewise find compositions that include plant species among their components, such as the one described in U.S. Pat. No. 5,916,565 that relates to a composition for veterinarian use made of 3 groups of components: a) flavoring additives, b) metabolic precursors for the biosynthesis of macro molecules necessary for the repair and maintenance of joint tissues, and c) phyto-chemicals selected from among 10 species, including *Curcuma longa* and *Harpagophytum procumbens*.

We can further mention U.S. Pat. No. 6,274,176 that describes an edible composition whose purpose is to serve as an anti-inflammatory agent in diseases such as arthritis and gout in mammals.

In this point, it is very important to mention that most of the phyto-compositions described in the previous art provide only an anti-inflammatory effect. It must, however, be stressed that other symptoms are present in arthritic diseases that have to be combated, such as pain, the appearance of subcutaneous nodules, joint immobility, reduction in muscular strength, etc., for which reason the phyto-compositions known in the previous art definitely have a limited scope.

Consequent to the foregoing, the search has been to eliminate the inconveniences of the usual drugs and phyto-compositions that are used in the treatment of joint diseases, developing a phyto-composition that is useful in reducing the inflammation of joints and that diminishes the pain involved in them and reduces the time stiffness or torpor time of the nodules or buttons that appear in the joints, and also allows the patient to improve in terms of muscle strength and greater mobility of his joints.

OBJECTS OF THE INVENTION

Taking into account the defects of the previous art, it is an object of this invention to provide a phyto-composition with a formula that is simple yet highly effective in the treatment of joint diseases, reducing inflammation and pain in the patients who suffer from them.

Another object of this invention is to provide a phyto-composition that provides a noticeable improvement in muscle strength and mobility of the affected joints in patients who suffer from the mentioned joint diseases.

It is another object of this invention to provide a pharmaceutical composition that includes the phyto-composition and a pharmaceutically acceptable vehicle such that it can be administered orally.

Still another object of this invention is the use of a pharmaceutical composition that includes the phyto-composition and that is useful in the treatment of joint diseases in humans by means of the administration of a therapeutically effective quantity of said pharmaceutical composition.

An additional object of this invention is to provide a pharmaceutical composition that includes the phyto-composition, which in conformity with its components and preparation method, is less expensive than the usual allopathic medications employed in the treatment of joint diseases.

DETAILED DESCRIPTION OF THE INVENTION

Surprisingly, it has been found that a phyto-composition prepared from extracts of *Curcuma longa* (curcuma), *Harpagophytum procumbens* (devil's claw), *Filipendula ulmaria* (meadowsweet) and oil of *Oenothera biennis* (onagra) has a synergic effect when used in the treatment of joint diseases, inasmuch as it provides anti-inflammatory, analgesic and immune modulator effects against the interleukins that intervene in this type of disease, allowing the patient to recover joint mobility and muscle strength.

The phyto-composition of this invention was conceived of in conformity with a particularly specific embodiment that must be considered illustrative only, and not restricted to said embodiment, and comprises in combination: (a) from 0.01% to 26% in weight of the total weight of an extract of *Curcuma longa*; (b) from 30% to 80% in weight of the total weight of an extract of *Harpagophytum procumbens*; (c) from 0.01% to 25% in weight of the total weight of an extract of Filipendula ulmaria; and (d) from 7% to 35% in weight of the total weight of oil of *Oenothera biennis*.

In an alternative embodiment of this invention, the phyto-composition comprises in combination: (a) from 0.01% to 15% in weight of the total weight of extract of *Curcuma longa*; (b) from 30% to 70% in weight of the total weight of the extract of *Harpagophytum procumbens*; (c) from 0.01% to 20% in weight of the total weight of the extract of *Filipendula ulmaria*; and (d) from 7% to 30% in weight of the total weight of oil of *Oenothera biennis*.

In relation to the species *Curcuma longa, Harpagophytum procumbens* and *Filipendula ulmaria*, it is appropriate to mention that the useful parts of said species from which such extracts are obtained, are the rhizome for *Curcuma longa* and *Harpagophytum procumbens*, while for *Filipendula ulmaria*, the flowers and leaves are used.

The extracts of these three species that form part of the phyto-composition of this invention are alcoholic extracts, aqueous extracts or hydroalcoholic extracts, hydroalcoholic extracts being used preferably in the specific embodiment of this invention. That is, they are prepared from a mixture of water and an alcohol, where said extracts are obtained through various procedures known in the previous art.

With respect to *Oenothera biennis*, its oil is obtained from the seeds of this plant by any of the methods known in the previous art.

Separately, for the administration to a patient of the phyto-composition that has been defined previously, the scope of this invention provides a pharmaceutical composition that comprises a therapeutically effective quantity of the phyto-composition in combination with a pharmaceutically acceptable vehicle, such that it can be administered preferably by oral route.

In an additional embodiment of this invention, the pharmaceutical composition is found in the pharmaceutical form of a soft gelatin capsule or an emulsion, and preferentially a water-oil emulsion.

Thus, the use of the phyto-composition of this invention in combination with a pharmaceutically acceptable vehicle permits the preparation of a pharmaceutical composition useful in the treatment of joint diseases in a mammal, particularly in the human being, said joint diseases consisting of rheumatoid arthritis, osteoarthritis, gouty arthritis, psoriatic arthritis, lupus and juvenile arthritis.

The pharmaceutical composition provides anti-inflammatory and analgesic effects and also makes it possible to lessen the time of rigidity, torpor and the pain of the nodules or buttons of the fingers or joints present in such diseases, permitting recovery of muscle strength.

As we have been mentioning, the pharmaceutical composition is used in patients with joint diseases in which the treatment consists of administering to a patient, a therapeutically effective quantity of a pharmaceutical composition that includes the phyto-composition of this invention exactly as has been defined previously. On this point, the joint diseases where it is possible to use the composition are those that were mentioned previously.

The phyto-composition for the treatment of joint diseases, as well as the pharmaceutical composition that is prepared from it, will be more clearly illustrated by means of the examples that are described below, which are presented for merely illustrative but not restrictive purposes, said examples being the following:

EXAMPLE 1

Preparation of the Phyto-Composition in Emulsion Pharmaceutical Form

Extracts of *Curcuma longa; Harpagophytum procumbens, Filipendula ulmadia* and oil of *Oenothera biennis* were weighted according to the following quantities respectively, 0.043 g, 14.77 g, 3.88 g and 6.91 g. Said weighed extracts were filtered additionally through an 80-micron mesh.

The extracts of *Harpagophytum procumbens* and *Filipendula ulmaria* were placed in a first stainless steel tank; 0.50 g of sodium methyl paraben and 0.060 g of sodium propyl paraben were also added; the contents of this tank were stirred manually until all the components were completely dissolved.

Separately, in a recipient containing 1.60 g of methyl cellulose, a quantity of bidistilled water was added and the contents of this recipient were heated to 80° C. with constant, manual stirring until forming a milky solution. At this moment, the recipient was removed from the heat source. The paste thus obtained was added to the first stainless steel tank where the extracts of *Harpagophytum procumbens* and *Filipendula ulmaria* were found already mixed with the sodium methyl paraben and the sodium propyl paraben.

The extract of *Curcuma longa* and the oil of *Oenothera biennis* were placed in a second stainless steel tank, where 30 ml were also added of cod liver oil and 1.5 g of an antioxidant known with the commercial name VEXEL. All the components of this second tank were mixed.

Additionally, 9 g of an emulsifier known under the commercial name of Canasol R4000H was heated in a double boiler, control of the temperature being maintained between 60 and 65° C. Said emulsifier was stirred manually until forming a clear, fluid solution which was later added to the second stainless steel tank, manual stirring being maintained. Later, a mechanical emulsifier (Silverson GX-15) was introduced into the tank to provide mechanical stirring of 2100 rpm.

The content of the first tank was added slowly and by intervals to the second tank, mechanical stirring being maintained with the Silverson emulsifier. Later, 1.2 g of a sweetener (Alitame) was added, after which bidistilled water was added, with mechanical stirring, the mixture being left to rest for 5 minutes. This last operation was repeated two more times, a water-oil emulsion being obtained ultimately, that incorporates the phyto-composition of this invention.

EXAMPLE 2

Clinical Study 65 people over 18 years of age (49 men and 16 women) who had been diagnosed with rheumatoid arthritis and osteoarthritis were submitted to a clinical study to observe the effects and benefits of using an emulsion of the phyto-composition of this invention.

In particular, the diagnosis of each disease was obtained by means of a clinical history, in which specific symptoms were looked for, for these diseases. In order for the diagnosis of rheumatoid arthritis to be made, the patient had to present at least four of the following symptoms: (1) morning rigidity in joints and neighboring zones lasting at least one hour before having the usual mobility; furthermore, this situation had to have presented for a minimum period of 4 to 6 weeks; (2) inflammation of soft tissues of three or more joints detected by a physician; the patients also had to have presented this situation for a minimum period of 4 to 6 weeks evolution; (3) inflammation of proximal interphalangeal, metacarpal-phalangeal joints, or of the wrist, for a minimum period of 4 to 6 weeks evolution; (4) subcutaneous nodules; (5) positive results in rheumatoid factor tests; and (6) erosions or periarticular osteopenia in joints of hands or wrists observed in x-rays.

For osteoarthritis, the following symptoms were looked for in the patients: i) pain in affected joints and that worsens with activity and improves with rest; (ii) morning rigidity iii) rigidity after periods of immobility; iv) augmentation of the size of the joints; v) joint instability; vi) limitation of joint mobility; vii) periarticular muscle atrophy; and viii) crepitations.

At the start and at the end of the treatment, lab tests and office studies were done in accordance with the diagnosis the patients presented, specifically, for patients with rheumatoid arthritis a complete rheumatic profile was done and antero-posterior (AP) and lateral x-rays were taken of the hands. For patients with osteoarthritis, mainly AP and lateral x-rays were taken of the affected joints.

The main criteria for inclusion in the clinical study were: patients over 18 years of age, men or women, with diagnosis of rheumatoid arthritis or osteoarthritis, in some cases, people with isolated symptoms such as joint pain, and in other cases, inclusion for treatment was determined depending on the type of arthropathy referred.

The criteria for non-inclusion were mainly patients with arthropathies related to other disorders, for example, systemic lupus erythematosis, arthropathies associated with hyper- or hypothyroidism, septic arthritis, among others, as well as people with gallbladder stones, people with active duodenal or gastric ulcer or who were in treatment for that reason.

The criteria for exclusion were for those patients who did not follow the treatment indications, shown in table 1.

TABLE 1

| CRITERIA FOR INCLUSION | CRITERIA FOR NON-INCLUSION | CRITERIA FOR EXCLUSION |
| --- | --- | --- |
| Men and women Over 18 years of age Any occupation Any marital status Any education Any socio-economic level Have accepted the treatment With diagnosis of rheumatoid arthritis or osteoarthritis With joint diseases without systemic complications Preferably with history of using various treatments for their illness | Under 18 years of age Pregnant and/or nursing Patients who were suspected or confirmed to have systemic damage or arthropathies related to systemic damage (systemic lupus erythematosis, arthropathies related to hyper- or hypothyroidism People with hypersensitivity to any of the components People who were using aspirin or Warfarin as anti-thrombosis therapy or any anticoagulant. | People who were using any substance or medication that could have had an influence on the treatment. Patients who did not follow the treatment instructions. People who used medications directed to limiting the disease or who were using steroid anti-inflammatory substances while under treatment with the emulsion. |

The patients who entered treatment received the phyto-composition of this invention, which was prepared in an emulsion pharmaceutical form exactly as described previously in example 1, in a dose of 45 ml per day administered in three parts. The emulsion was dissolved in water and administered by oral route to patients after meals for 90 continuous days. After this period, it was observed in general that 90% of the patients experienced temporary worsening at the start of treatment, mainly in the joints most affected by their disease, that is, where there was greater inflammation and the most tissue damage. This temporary worsening lasted on average 11 days (minimum 7 and maximum 15 days). However, there was very considerable reduction in inflammation and pain after this time.

It is even more important to point out that during this worsening phase, it was noted that the patients did not reduce their consumption of analgesics, but after this temporary worsening phase, 75% of the patients stopped using them.

This significant reduction both in inflammation and in pain, gave the patients mobility of the affected joints. In addition, the patients recovered the muscle strength that the inflammation and pain had affected.

Separately, it was also observed that the patients who presented nodules with different characteristics and in different locations, and which were very painful on the least contact, also experienced change in them: Their size diminished in 50% of the patients and the pain disappeared in 90% of the cases.

In all the cases, the morning rigidity or general rigidity diminished at a rate of 80 to 90% in the patients. The patients who entered with diagnoses of circulatory disorders also showed improvement in their symptoms.

Concerning secondary reactions, 5 women presented slight diarrhea at the start of treatment, but none abandoned treatment. One woman was excluded from the treatment because she used self-prescribed medications that contained steroids. Two patients abandoned the treatment due to the temporary worsening reaction despite the fact that these patients were not those who experienced the most intense worsening. It is also important to point out that the patients never said that the temporary worsening reaction was a problem of disability for them.

Of the total patients, 62 completed the treatment; of these, 75.8% (47 patients) did not present symptoms related to the joint disease.

Moreover, 15 patients mentioned that the pain they experienced after treatment was slight and was controlled relatively easily with analgesics and/or anti-inflammatory agents of the non-steroid type, in low doses, and with intermittent use. The patients also mentioned that their consumption of these analgesics and/or anti-inflammatory agents diminished by 65-70% below the amount they were taking prior to treatment with the emulsion prepared in accordance with this invention.

It should be pointed out that patients entered the study who had major joint deformities, but in particular, it is important to mention that although these deformities were not corrected, there was improvement with respect to reduced pain and inflammation, diminished joint rigidity, and this allowed them to engage again in activities that had already been interrupted, such as feeding themselves, something that the patients expressed as greatly beneficial to them. It is very important to highlight in the foregoing, the reaction called temporary worsening, which exactly as mentioned previously, manifested in 90% of the patients treated shortly after the start of treatment, which worsening consisted of pain in the joints most affected by the disease, the most inflamed or the most deformed ones. The pain was the stabbing kind (pricking, jabbing) that lasted for a few instants and disappeared, but this was part of the therapeutic action on the joints by the pharmaceutical composition of this invention.

Exactly as was seen in the clinical study, once this temporary crisis had been overcome, the joint inflammation and pain diminished progressively, allowing the patients to recover mobility of the joints and reducing the rigidity or torpor time.

This temporary worsening manifestation is a particular situation and had not been observed previously for another type of phyto medicament, and is considered part of the therapeutic process of the phyto-composition and the pharmaceutical composition.

Furthermore, said worsening could not have been inferred from the individual action of each one of the species that form the phyto-composition. In other words, the components of the phyto-composition acted in an unexpected, synergic manner, results being obtained that cannot be deduced obviously by an expert with knowledge in the subject matter.

For example, although it is true that the species *Curcuma longa* and *Harpagophytum procumbens* have anti-inflammatory effects, the pharmaceutical composition with the phyto-composition of this invention had a more obvious anti-inflammatory effect than that observed fro said species in isolation. Besides, the clinical pattern of the diseases was modified, particularly because of the following:

a) The joint inflammation and pain diminished progressively.
b) The time of rigidity or torpor diminished
c) The pain of the nodules or "buttons" diminished in the fingers or in any other of the joints, and in some cases they diminished in size.
d) The muscle strength was gradually recovered, allowing the patients affected by the joint disease to perform daily activities with greater confidence and security and in most cases without having had to use analgesics and/or anti-inflammatory agents to control pain and inflammation.

As can also be observed, the adverse effects presented by the use of the pharmaceutical composition of this invention are minimal or nil, particularly when compared with the adverse effects presented by DMDs.

On the other hand, it is obvious from all points of view that the pharmaceutical composition that is described in the embodiments of this invention costs less than the allopathic medications used in the treatment of joint diseases.

In keeping with the foregoing description, it will be observed that the phyto-composition for treatment of joint disease of this invention, as well as the pharmaceutical composition prepared with it, were conceived to assist in the treatment of this type of disease, and more specifically, in rheumatoid arthritis and osteoarthritis, helping to manifest improvement in joint strength and mobility in an extremely effective manner. It is important to point out that innumerable modifications can be made to the pharmaceutical composition of this invention, such as may be the concentration of the 4 basic species that comprise it, and the pharmaceutical form that permits its administration to a patient, among other things.

Even though reference has been made in the foregoing description to certain embodiments of this invention, it must be emphasized that numerous modifications to such embodiments are possible, without departing from the true scope of the invention. Therefore, this invention must not be restricted except by what is established in the state of the art, as well as by the attached claims.

The invention claimed is:

1. A phyto-composition comprising in combination: (a) extract of *Curcuma longa*; (b) extract of *Harpagophytum procumbens*; (c) extract of *Filipendula ulmaria*; and d) oil of *Oenothera biennis*,
    wherein the extracts and the oil respectively are present in the phyto-composition in the following percentage in weight concentrations with respect to the total weight of the composition: (a) from 0.01% to 26% of the extract of *Curcuma longa*; (b) from 30% to 80% of the extract of *Harpagophytum procubens*; (c) from 0.01% to 25% of the extract of *Filipendula ulmaria*; and (d) from 7 to 35% of the oil of *Oenothera biennis*.

2. A phyto-composition according to claim 1, wherein the extracts and oil respectively are present in the phyto-composition in the following percentage in weight concentrations with respect to the total weight of the composition: (a) from 0.01% to 15% of the extract of *Curcuma lonra*; (b) from 30% to 70% of the extract of *Harpagophytum procumbens*; (c) from 0.01% to 20% of the extract of *Filipendula ulmaria*; and d) from 7% to 30% of the oil of *Oenothera biennis*.

3. A phyto-composition according to claim 1, wherein the extracts of *Curcuma longa, Harpagophytum procumbens*; and *Filipendula ulmaria*; are aqueous, alcoholic or hydro-alcoholic extracts.

4. A phyto-composition according to claim 3, wherein the extracts are hydro-alcoholic.

5. A pharmaceutical composition comprising a therapeutically effective quantity of the phyto-composition as claimed in claim 1 in combination with a pharmaceutically acceptable vehicle.

6. A pharmaceutical composition according to claim 5, wherein the pharmaceutical composition is formulated to be administered orally.

7. A pharmaceutical composition according to claim 5, wherein the pharmaceutical composition is in the form of an emulsion or a soft gelatin capsule.

8. A pharmaceutical composition according to claim 7, wherein the emulsion is a water-oil emulsion.

9. A method for treating a joint disease in a patient in need thereof comprising administering to the patient an effective amount of the pharmaceutical composition according to claim 5.

10. The method according to claim 9, wherein the joint disease is rheumatoid arthritis, osteoarthritis, gouty arthritis, psoriatic arthritis, lupus or juvenile arthritis,
    said method providing anti-inflammatory and analgesic effects, as well as the progressive reduction in time of rigidity, torpor and pain of the nodules or buttons of the fingers or joints present in such diseases, besides permitting recovery of muscle strength.

11. The method according to claim 10, wherein the joint disease is rheumatoid arthritis or osteoarthritis.

* * * * *